United States Patent
Rulkov et al.

(10) Patent No.: US 9,504,393 B1
(45) Date of Patent: *Nov. 29, 2016

(54) MONITORING DEVICE, METHOD AND SYSTEM

(71) Applicant: Impact Sports Technologies, Inc., San Diego, CA (US)

(72) Inventors: Nikolai Rulkov, San Diego, CA (US); Donald Brady, Las Vegas, NV (US); Mark Hunt, San Diego, CA (US); Sammy Elhag, San Diego, CA (US); Steve Lui, San Diego, CA (US)

(73) Assignee: Impacts Sports Technologies, Inc., San Diego, CA (US)

( * ) Notice: Subject to any disclaimer, the term of this patent is extended or adjusted under 35 U.S.C. 154(b) by 216 days.

This patent is subject to a terminal disclaimer.

(21) Appl. No.: 14/262,771

(22) Filed: Apr. 27, 2014

Related U.S. Application Data

(60) Continuation of application No. 13/026,266, filed on Feb. 13, 2011, now Pat. No. 8,708,918, which is a division of application No. 11/473,641, filed on Jun. 24, 2006, now Pat. No. 7,887,492, which is a continuation-in-part of application No. 11/085,778, filed on Mar. 21, 2005, now abandoned.

(60) Provisional application No. 60/613,785, filed on Sep. 28, 2004.

(51) Int. Cl.
*A61B 5/02* (2006.01)
*A61B 5/024* (2006.01)
*A61B 5/11* (2006.01)

(52) U.S. Cl.
CPC .......... *A61B 5/02427* (2013.01); *A61B 5/1118* (2013.01)

(58) Field of Classification Search
USPC ................................ 600/485–515
See application file for complete search history.

*Primary Examiner* — Michael Kahelin
*Assistant Examiner* — Mitchell E Alter
(74) *Attorney, Agent, or Firm* — Clause Eight IPS; Michael Catania

(57) ABSTRACT

A monitoring device (20) and method (200) for monitoring the health of a user is disclosed herein. The monitoring device (20) is preferably an article (25), an optical sensor (30), a circuitry assembly (35) a display member (40) and a control component (43). The monitoring device (20) preferably displays the following information about the user: pulse rate; calories expended by the user of a pre-set time period; target zones of activity; time; and distance traveled.

4 Claims, 8 Drawing Sheets

MONITORING DEVICE, METHOD AND SYSTEM

CROSS REFERENCES TO RELATED APPLICATIONS

The Present Application is a continuation application of U.S. patent application Ser. No. 13/026,266, filed on Feb. 13, 2011, which is a divisional application of U.S. patent application Ser. No. 11/473,641, filed on Jun. 24, 2006, now U.S. Pat. No. 7,887,492, issued on Feb. 15, 2011, which is a continuation-in-part application of U.S. patent application Ser. No. 11/085,778, filed on Mar. 21, 2005, now abandoned, which claims priority to U.S. Provisional Application No. 60/613,785 filed on Sep. 28, 2004.

STATEMENT REGARDING FEDERALLY SPONSORED RESEARCH OR DEVELOPMENT

Not Applicable

BACKGROUND OF THE INVENTION

Field of the Invention

The present invention is related to health monitoring devices. More specifically, the present invention relates to a glove for monitoring a user's vital signs.

Description of the Related Art

There is a need to know how one is doing from a health perspective. In some individuals, there is a daily, even hourly, need to know one's health. The prior art has provided some devices to meet this need.

One such device is a pulse oximetry device. Pulse oximetry is used to determine the oxygen saturation of arterial blood. Pulse oximeter devices typically contain two light emitting diodes: one in the red band of light (660 nanometers) and one in the infrared band of light (940 nanometers). Oxyhemoglobin absorbs infrared light while deoxyhemoglobin absorbs visible red light. Pulse oximeter devices also contain sensors that detect the ratio of red/infrared absorption several hundred times per second. A preferred algorithm for calculating the absorption is derived from the Beer-Lambert Law, which determines the transmitted light from the incident light multiplied by the exponential of the negative of the product of the distance through the medium, the concentration of the solute and the extinction coefficient of the solute.

The major advantages of pulse oximetry devices include the fact that the devices are non-invasive, easy to use, allows for continuous monitoring, permits early detection of desaturation and is relatively inexpensive. The disadvantages of pulse oximetry devices are that it is prone to artifact, it is inaccurate at saturation levels below 70%, and there is a minimal risk of burns in poor perfusion states. Several factors can cause inaccurate readings using pulse oximetry including ambient light, deep skin pigment, excessive motion, fingernail polish, low flow caused by cardiac bypass, hypotension, vasoconstriction, and the like.

Chin et al., U.S. Pat. No. 6,018,673 discloses a pulse oximetry device that is positioned entirely on a user's nail to reduce out of phase motion signals for red and infrared wavelengths for use in a least squares or ratio-of-ratios technique to determine a patient's arterial oxygen saturation.

Smith, U.S. Pat. No. 4,800,495 discloses an apparatus for processing signals containing information concerning the pulse rate and the arterial oxygen saturation of a patient. Smith also discloses maintaining the position of the LEDs and detectors to prevent motion-artifacts from being produced in the signal.

Another method for using a pulse oximeter to measure blood pressure is disclosed in U.S. Pat. No. 6,616,613 to Goodman for a 'Physiological Signal Monitoring System'. The '613 Patent discloses processing a pulse oximetry signal in combination with information from a calibrating device to determine a patient's blood pressure.

Chen et al, U.S. Pat. No. 6,599,251 discloses a system and method for monitoring blood pressure by detecting pulse signals at two different locations on a subjects body, preferably on the subject's finger and earlobe. The pulse signals are preferably detected using pulse oximetry devices.

Schulze et al., U.S. Pat. No. 6,556,852, discloses the use of an earpiece having a pulse oximetry device and thermopile to monitor and measure physiological variables of a user.

Malinouskas, U.S. Pat. No. 4,807,630, discloses a method for exposing a patient's extremity, such as a finger, to light of two wavelengths and detecting the absorbance of the extremity at each of the wavelengths.

Jobsis et al., U.S. Pat. No. 4,380,240 discloses an optical probe with a light source and a light detector incorporated into channels within a deformable mounting structure which is adhered to a strap. The light source and the light detector are secured to the patient's body by adhesive tapes and pressure induced by closing the strap around a portion of the body.

Tan et al., U.S. Pat. No. 4,825,879 discloses an optical probe with a T-shaped wrap having a vertical stem and a horizontal cross bar, which is utilized to secure a light source and an optical sensor in optical contact with a finger. A metallic material is utilized to reflect heat back to the patient's body and to provide opacity to interfering ambient light. The sensor is secured to the patient's body using an adhesive or hook and loop material.

Modgil et al., U.S. Pat. No. 6,681,454 discloses a strap that is composed of an elastic material that wraps around the outside of an oximeter probe and is secured to the oximeter probe by attachment mechanisms such as Velcro, which allows for adjustment after initial application without producing excessive stress on the spring hinge of the oximeter probe.

Diab et al., U.S. Pat. No. 6,813,511 discloses a disposable optical probe suited to reduce noise in measurements, which is adhesively secured to a patient's finger, toe, forehead, earlobe or lip.

Diab et al., U.S. Pat. No. 6,678,543 discloses an oximeter sensor system that has a reusable portion and a disposable portion. A method for precalibrating a light sensor of the oximeter sensor system is also disclosed.

Tripp, Jr. et al., U.S. Statutory Invention Registration Number H1039 discloses an intrusion free physiological condition monitor that utilizes pulse oximetry devices.

Hisano et al., U.S. Pat. No. 6,808,473, discloses a headphone-type exercise aid which detects a pulse wave using an optical sensor to provide a user with an optimal exercise intensity.

Mathews, U.S. Pat. No. 5,431,170 ("Mathews"), discloses a pulse responsive device, which has a pulse oximetry device (10) attached to a headband (12) and a separate read-out device (14) that may be attached to a glove and worn on the user's hand. Mathews discloses that the read-out device (14) has a digital display and an analogue display, however, Mathews provides no further detail.

Mault et al, U.S. Patent Application Publication Number 2002/0109600 ("Mault") discloses a smart activity monitor ("SAM") which is a pedometer based device which includes an electronic clock, a sensor, entry means for recording food consumption and exercise activities and a memory for storing such information. Mault fails to disclose the details of the display other than to mention that the SAM has a time display, an exercise display and a food display, with the exercise and food displays having a bar-graph style. Mault fails to disclose an optical sensor in detail, and only states that photo-plethysmography may be used to determine the heart rate by a sensor provided on the rear of a wrist mounted SAM.

Kopotic et al, U.S. Pat. No. 6,470,199, discloses a sock for positioning an optical probe.

Yasukawa et al., U.S. Pat. No. 5,735,800 ("Yasukawa"), discloses a wrist-worn device which is intended for limited motion about the user's wrist. Yasukawa discloses an optical sensor that uses a blue LED with a phototransistor in conjunction with an analog to digital converter to provide a digital signal to a data processing circuit.

In monitoring one's health there is a constant need to know how many calories have been expended whether exercising or going about one's daily routine. A calorie is a measure of heat, generated when energy is produced in our bodies. The amount of calories burned during exercise is a measure of the total amount of energy used during a workout. This can be important, since increased energy usage through exercise helps reduce body fat. There are several means to measure this expenditure of energy. To calculate the calories burned during exercise one multiplies the intensity level of the exercise by one's body weight (in kilograms). This provides the amount of calories burned in an hour. A unit of measurement called a MET is used to rate the intensity of an exercise. One MET is equal to the amount of energy expended at rest.

For example, the intensity of walking 3 miles per hour ("mph") is about 3.3 METS. At this speed, a person who weighs 132 pounds (60 kilograms) will burn about 200 calories per hour (60×3.3=198).

The computer controls in higher-quality exercise equipment can provide a calculation of how many calories are burned by an individual using the equipment. Based on the workload, the computer controls of the equipment calculate exercise intensity and calories burned according to established formulae.

The readings provided by equipment are only accurate if one is able to input one's body weight. If the machine does not allow this, then the "calories per hour" or "calories used" displays are only approximations. The machines have built-in standard weights (usually 174 pounds) that are used when there is no specific user weight.

There are devices that utilize a watch-type monitor to provide the wearer with heart rate as measured by a heart-beat sensor in a chest belt.

The prior art has failed to provide a means for monitoring one's health that is accurate, easy to wear on one's body for extended time periods, allows the user to input information and control the output, and provides sufficient information to the user about the user's health. Thus, there is a need for a monitoring device that can be worn for an extended period and provide health information to a user.

BRIEF SUMMARY OF THE INVENTION

The present invention provides a solution to the shortcomings of the prior art. The present invention is accurate, comfortable to wear by a user for extended time periods, allows for input and controlled output by the user, is light weight, and provides sufficient real-time information to the user about the user's health.

One aspect of the present invention is a monitoring device for monitoring the health of a user. The monitoring device includes an article, an optical device for generating a pulse waveform, a circuitry assembly embedded within the article, a display member positioned on an exterior surface of the article, and a control means attached to the article.

The article preferably has a main body and thumb portion. The article preferably has a minimal mass, one to five ounces, and is flexible so that the user can wear it the entire day if necessary. The monitoring device allows the user to track calories burnt during a set time period, monitor heart rate, blood oxygenation levels, distance traveled, target zones and optionally dynamic blood pressure.

Another aspect of the present invention is a method for monitoring a user's vital signs. The method includes generating a digital signal corresponding to the flow of blood through an artery of the user. The signal is generated from an optical device. Next, the heart rate data of the user of the user is generated from the digital signal. Next, the heart rate data of the user is processed for analysis of calories expended by the user and for display of the user's heart rate and other information. Next, the calories expended by the user, the user's heart rate or the user's blood oxygen saturation level are displayed on a display member on an exterior surface of an article, which is controlled by the user using a control component extending from the article.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
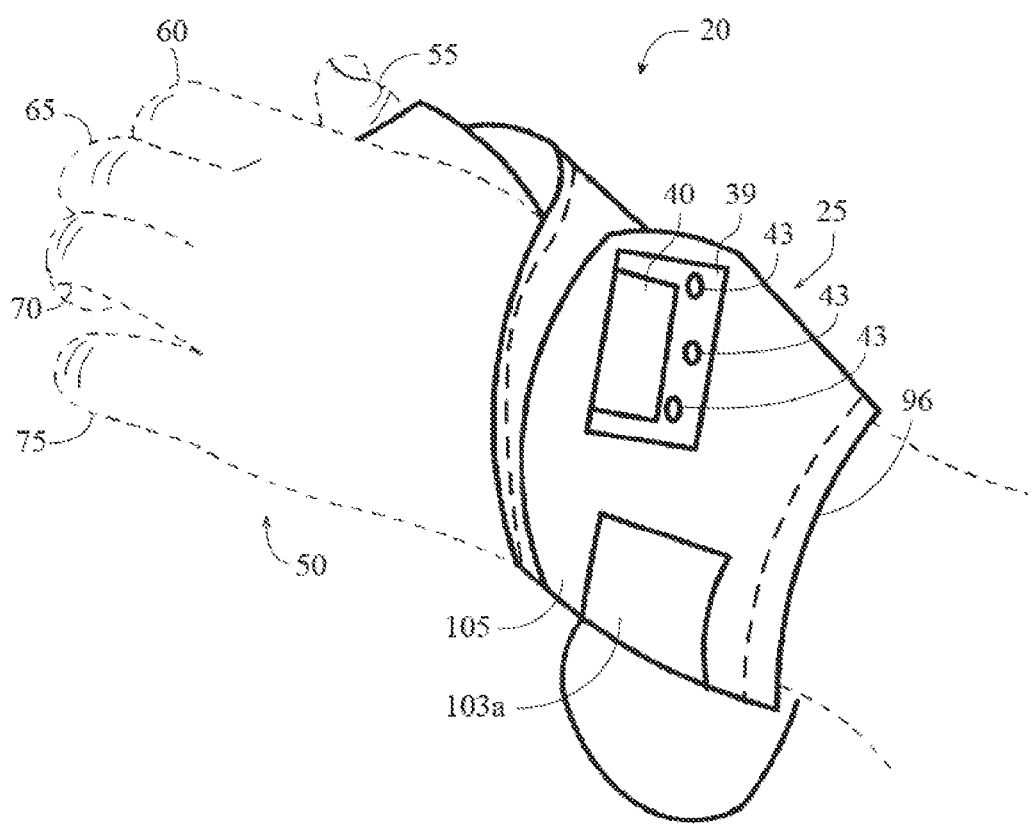
FIG. 1 is a perspective view of a preferred embodiment of a monitoring device worn by a user.
Figure 2:
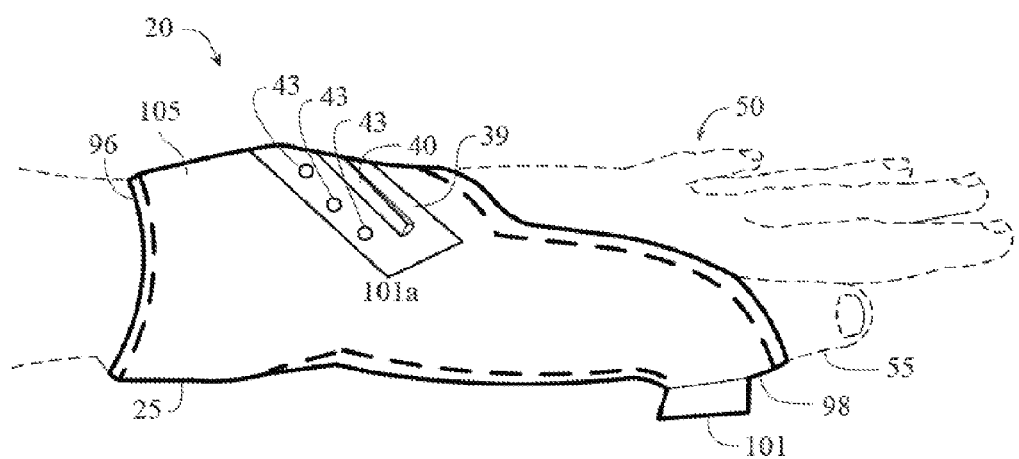
FIG. 2 is a palm side view of the monitoring device of FIG. 1 worn by the user.
Figure 3:
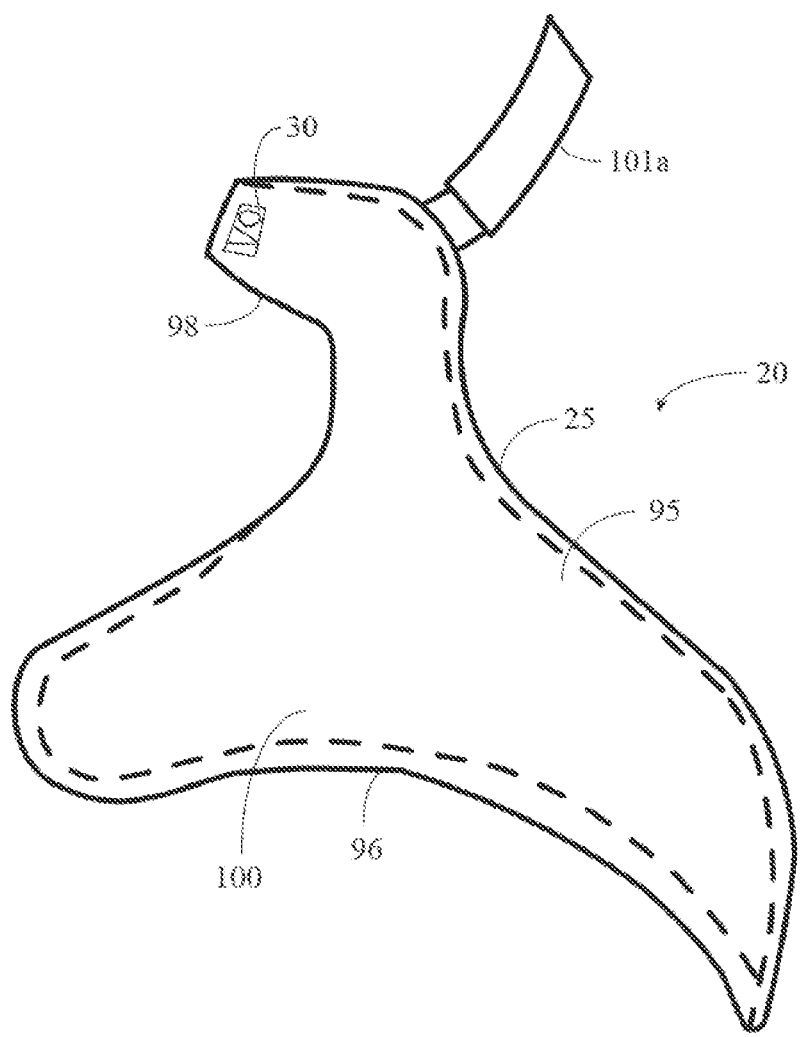
FIG. 3 is a plan view of a preferred embodiment of an interior surface monitoring device of FIG. 1 unattached to a user's hand.

As shown in FIGS. 1-5B, a monitoring device is generally designated 20. The monitoring device 20 preferably includes an article 25, an optical sensor 30, a circuitry assembly 35, a display member 40, a control component 43a-c and connection wires 45. The monitoring device 20 is preferably worn on a user's hand 50.

The article 25 preferably has a main body portion 95 and a thumb portion 98. The main body portion 95 preferably has a palm portion 100 that covers a portion of the user's palm 80 and a back portion 105 that covers the back 85 of the user's hand 50. Preferably, an annular portion 98a of the thumb portion 98 of the article is wrapped around the user's thumb 55. An attachment means 101 of the annular portion 98a is used to secure the thumb portion 98 around the user's thumb 55.

An attachment means 103 is used to secure a flap portion 100a of the palm portion 100 to a flap portion 105a of the back portion 105. A first part 103a of the attachment means 103 is positioned on the flap portion 100a and a second part 103b of the attachment means 103 is positioned on the flap portion 105a. In a preferred embodiment, a VELCRO® material is utilized as the attachment means 103 and attachment means 101.

It is desirous to adapt the article 25 to the anatomy of the user's hand 50. The article 25 is preferably composed of leather, synthetic leather, LYCRA, another similar material, or a combination thereof. The back portion 105 has an exterior surface preferably having a sealable board pocket 112. The article 25 preferably has a mass ranging from 5 grams to 50 grams, more preferably from 10 grams to 25 grams, and most preferably 17 grams. Preferably, the lower the mass of the article 25, the more comfort to the user. The article 25 preferably has a thickness of less than 0.5 centimeters, and preferably ranges from 0.5 centimeters to 0.1 centimeters. The total monitoring device preferably has a mass ranging from 7 grams to 60 grams, and more preferably from 10 grams to 30 grams.

The main body 95 has a wrist edge 96 that preferably defines a lower portion of the article 25. Substantially perpendicular to the wrist edge 96 is a first edge 97a and a second edge 97b. The thumb portion 98 is preferably integral with the main body 95 and preferably is positioned at an upper part of the main body 95 opposite the wrist edge 96. The wrist edge preferably has a length ranging from 15 centimeters to 40 centimeters, and more preferably from 20 centimeters to 30 centimeters. The main body has a width, W, that ranges from 4 centimeters to 8 centimeters and is most preferably 5 centimeters to 6 centimeters. A top of the thumb portion 98 preferably extends from 14 centimeters to 25 centimeters from the wrist edge 96, and more preferably from 16 centimeters to 20 centimeters.

The optical sensor is preferably positioned on the thumb portion 98 and connected to the circuitry assembly by the connection wires 45. The connection wires 45 are preferably embedded within the main body 95 and thumb portion 98.

In a preferred embodiment, the optical sensor 30 is a photodetector 130 and a single light emitting diode ("LED") 135 transmitting light at a wavelength of approximately 660 nanometers. As the heart pumps blood through the arteries in the user's ear, blood cells absorb and transmit varying amounts of the light depending on how much oxygen binds to the cells' hemoglobin. The photodetector 30, which is typically a photodiode, detects transmission at the red wavelengths, and in response generates a radiation-induced signal.

Alternatively, the optical sensor 30 is a pulse oximetry device with a light source 135 that typically includes LEDs that generate both red ($\lambda$~660 nm) and infrared ($\lambda$~900 nm) radiation. As the heart pumps blood through the arteries in the hand of the user, blood cells absorb and transmit varying amounts of the red and infrared radiation depending on how much oxygen binds to the cells' hemoglobin. The photodetector 130, which is typically a photodiode, detects transmission at the red and infrared wavelengths, and in response generates a radiation-induced signal. Yet in an alternative embodiment, the optical device 30 is based on green light wherein a LED generates green light ($\lambda$~500-600 nm), and the photodetector detects the green light.

Figure 12:
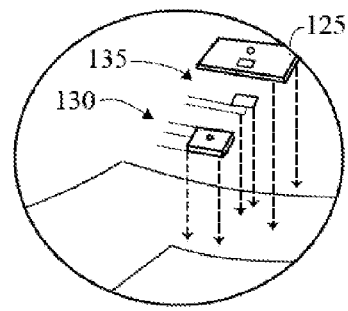
FIG. 12 is an isolated exploded view of an optical sensor and thumb portion of an article of the monitoring device.

As shown in FIG. 12, the optical sensor 30 preferably has a body 125 to cover a photo-detector 130 and a light source 135 on the thumb portion 98. The body 125 is preferably composed of a material similar to the thumb portion 98.

Alternatively, the optical sensor 30 is pulse oximetry device comprising the photo-detector 130, a first light source 125 and a second light source 125a, not shown. In this embodiment, the first light source 125 emits light in an infrared range ($\lambda$~900 nm) and the second light source 125a emits light in a red range ($\lambda$~630 nm). In either embodiment, placement of the optical sensor 30 is preferably in a lower portion of the user's index finger 60. Alternatively, the optical sensor 30 placed at a fingertip of the user. Further, the optical sensor 30 need only be in proximity to an artery of the user in order to obtain a reading or signal. In an alternative embodiment, the finger portion 98 and optical sensor do not contact the finger of the user and only circle the finger of the user.

The light source 135 typically is a light-emitting diode that emits light in a range from 600 nanometers to 1100 nanometers. As the heart pumps blood through the patient's finger, blood cells absorb and transmit varying amounts of the red and infrared radiation depending on how much oxygen binds to the cells' hemoglobin. The photodetector 30, which is typically a photodiode, detects transmission at the red and infrared wavelengths, and in response generates a radiation-induced current that travels through the connection wires 45 to the circuitry assembly 35 on the article 25.

A preferred photodetector 130 is a light-to-voltage photodetector such as the TSL260R and TSL261, TSL261R photodetectors available from TAOS, Inc of Plano Tex. Alternatively, the photodetector 130 is a light-to-frequency photodetector such as the TSL245R, which is also available from TAOS, Inc. The light-to-voltage photodetectors have an integrated transimpedance amplifier on a single monolithic integrated circuit, which reduces the need for ambient light filtering. The TSL261 photodetector preferably operates at a wavelength greater than 750 nanometers, and optimally at 940 nanometers, which would preferably have a LED that radiates light at those wavelengths. A preferred optical sensor 30 utilizing green light is a TRS1755 sensor from TAOS, Inc of Plano Tex. The TRS1755 comprises a green LED light source (567 nm wavelength) and a light-to-voltage converter. The output voltage is directly proportional to the reflected light intensity.

In a preferred embodiment, the circuit assembly 35 is flexible to allow for the contour of the user's hand and movement thereof. Preferably the dimensions of a board of the circuit assembly 35 are approximately 39 millimeters (length) by approximately 21 millimeters (width) by 0.5 millimeters (thickness).

Figure 7:
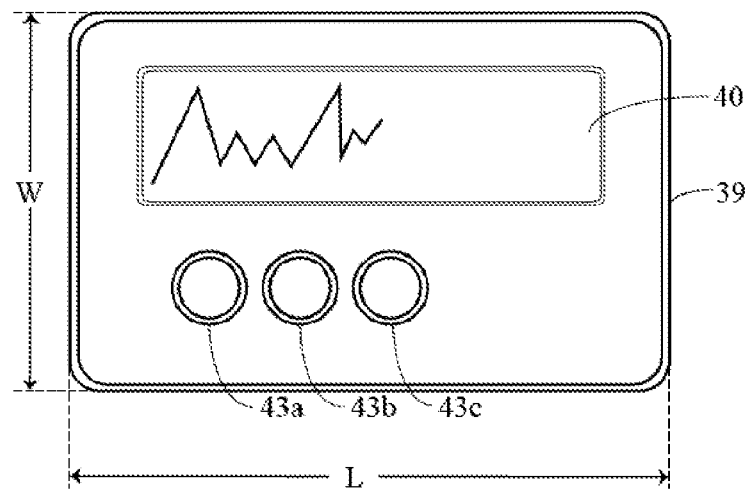
FIG. 7 is an isolated view of a preferred embodiment of a circuit board housing of the monitoring device.

As shown in FIG. 7, the length, "L" of the circuitry assembly housing 39 ranges from 30 millimeters to 50 millimeters, more preferably from 40 millimeters to 44 millimeters, and is most preferably approximately 42 millimeters. The width, "W" of the circuitry assembly housing 39 ranges from 20 millimeters to 40 millimeters, more preferably from 25 millimeters to 30 millimeters, and is most preferably approximately 27 millimeters. The thickness of the circuitry assembly housing 39 ranges from 0.5 millimeter to 3 millimeters, more preferably from 1 millimeter to 2 millimeters, and is most preferably approximately 1.5 millimeters.

Alternatively, the circuitry assembly 35 includes a flexible microprocessor board and a flexible pulse oximetry board. An alternative pulse oximetry board is a BCI MICRO POWER oximetry board, which is a low power, micro-size easily integrated board which provides blood oxygenation level, pulse rate (heart rate), signal strength bargraph, plethysmogram and status bits data. The size of the board is preferably 25.4 millimeters (length)×12.7 millimeters (width)×5 millimeters (thickness). The microprocessor board receives data from the pulse oximetry board and processes the data to display on the display member 40. The microprocessor can also store data. The microprocessor can process the data to display pulse rate, blood oxygenation levels, calories expended by the user of a pre-set time period, target zone activity, time and dynamic blood pressure. Alternatively, the circuitry assembly 35 is a single board with a pulse oximetry circuit and a microprocessor.

Figure 10:
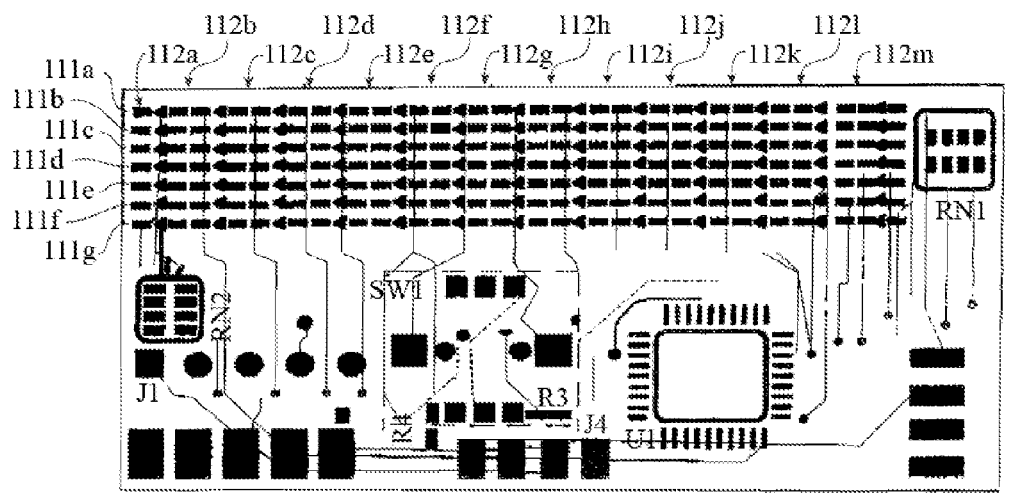
FIG. 10 is a schematic diagram of combined circuit assembly and display member utilized with the monitoring device.

The display member 40 is preferably a light emitting diode ("LED"). Alternatively, the display member 40 is a liquid crystal display ("LCD") or other similar display device. As shown in FIG. 10, the display member 40 is an LED array which preferably has seven rows 111a-111g and thirteen columns 112a-112r. The LED array allows for each column to be illuminated separately thereby giving the appearance of a moving display. For example, if the term "200 calories expended" is displayed on the display member 40, the "2" of the "200" would preferably first appear in column 112m and then subsequently in each of the other columns 1121-112a, from the right-most column to the left-most column thereby giving the appearance of the term scrolling along the display member 40. The terms or words alternatively scroll from left to right. Still alternatively, all of the columns are illuminated at once or all flash in strobe like manner. Further, a real-time pulse waveform of the user is displayed as the default on the display member 40 as shown in FIG. 7. Those skilled in the pertinent art will recognize alternative methods of displaying information on the display member 40 without departing from the scope and spirit of the present invention.

Figure 8:
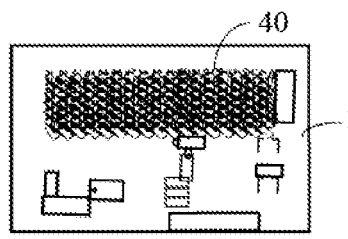
FIG. 8 is a schematic view of the circuitry of the circuit board of the monitoring device.
Figure 9:
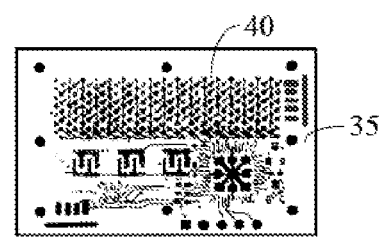
FIG. 9 is a schematic view of the circuitry of the circuit board of the monitoring device.

As shown in FIGS. 8-10, the display member 40 is preferably combined with the circuit assembly 35. A microcontroller 41 processes the signal generated from the optical sensor 30 to generate the plurality of vital sign information for the user which is displayed on the display member 40. The control means 43 is connected to the circuit assembly 35 to control the input of information and the output of information displayed on the display member 40.

Figure 5:
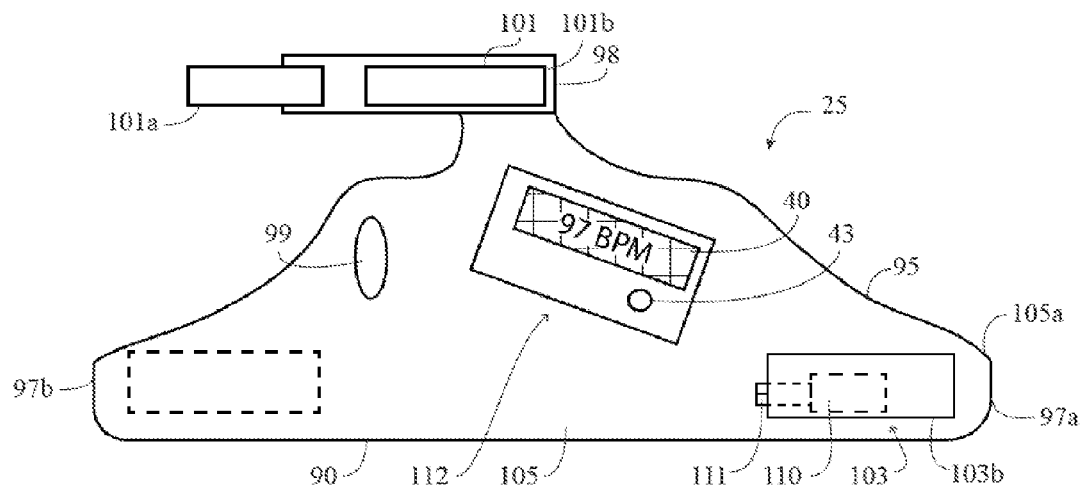
FIG. 5 is a plan view of an exterior surface of an alternative embodiment of the monitoring device.
Figure 6:
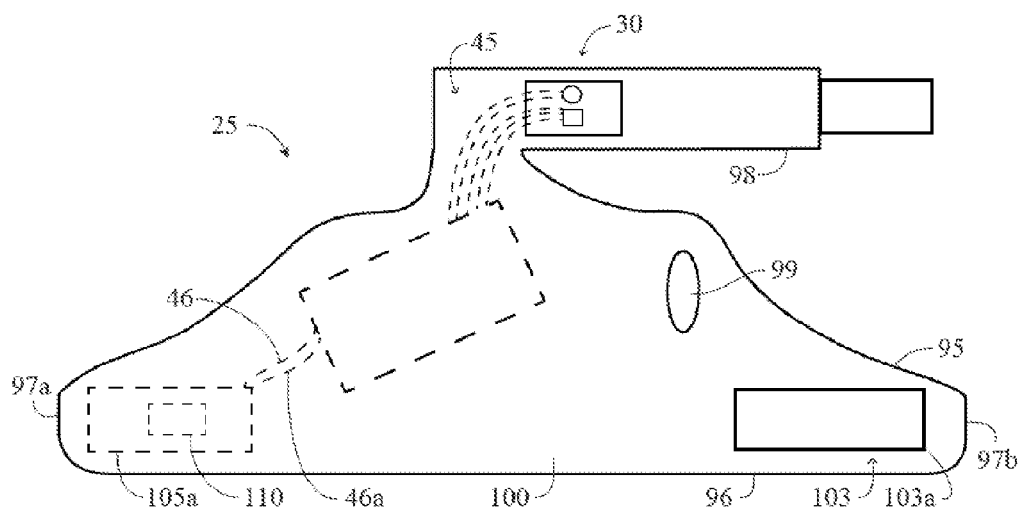
FIG. 6 is a plan view of an interior surface of an alternative embodiment of the monitoring device.

FIG. 5 illustrates an alternative embodiment of the control component 43. The control component 43 preferably has a body with a top. The body preferably has a shape which minimizes mass and is easily operated by the user. The control component 43 in the alternative embodiment is preferably a button or "joystick" that is capable of multiple dimensional movement such as being compressible up and down. The multiple dimensional movement of the control component 43 allows for the user to enter or select functions and scroll through menus which are displayed on the display member 40, as discussed below.

Figure 11:
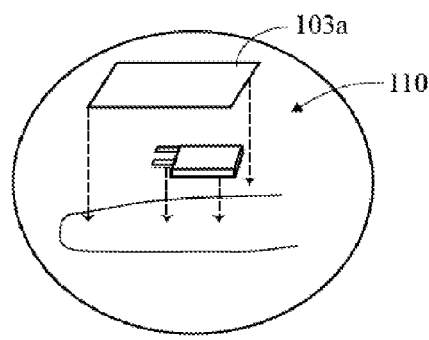
FIG. 11 is an isolated exploded view of a power source and flap portion of an article of the monitoring device.

The monitoring device 20 is preferably powered by a power source 110 which is preferably positioned on the flap portion 105a of the back portion 105 of the article 25. In a preferred embodiment, as shown in FIG. 11, the power source 110 is placed under the second part 103b of the attachment means 103. Preferably the power source 110 is a battery. The power source 110 is preferably connected to the circuit assembly 35 by positive wire 46 and ground wire 47, and the ground wire 47 and positive wire 46 are embedded within the article 25. The power source 110 is preferably a lithium ion rechargeable battery such as available from NEC-Tokin. The power source preferably has an accessible port 11 for recharging. The circuit assembly 35 preferably requires 5 volts and draws a current of 20- to 40 milliamps. The power source 110 preferably provides at least 900 milliamp hours of power to the monitoring device 20.

Figure 4:
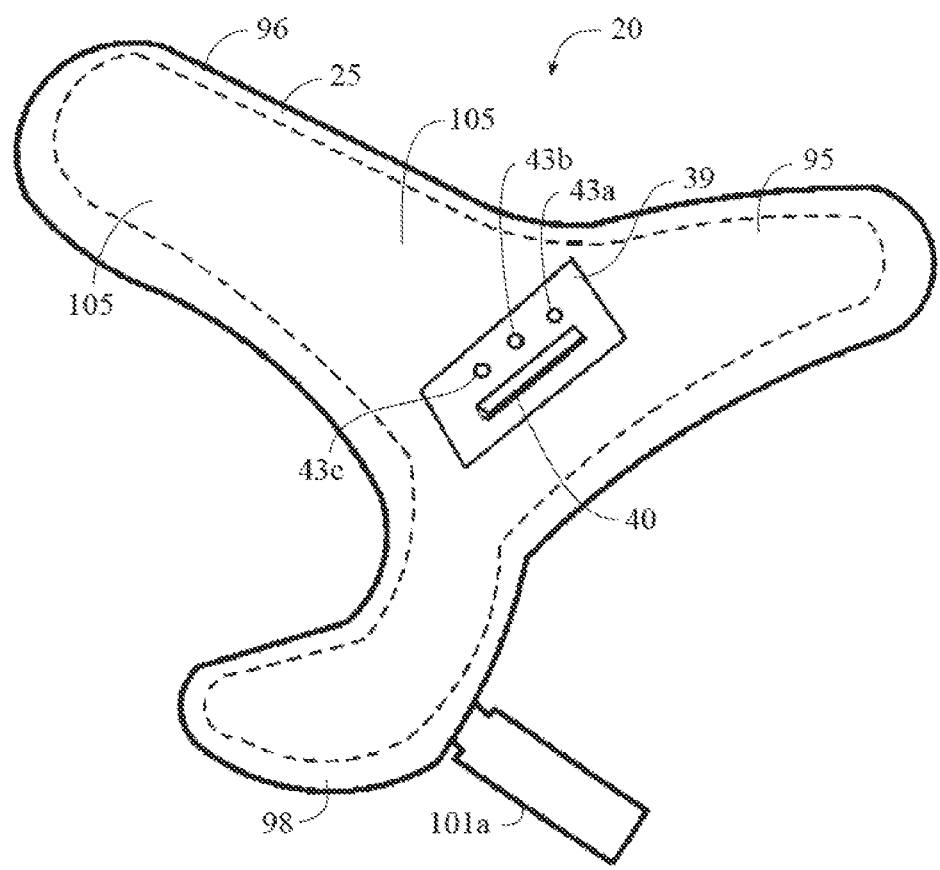
FIG. 4 is a plan view of a preferred embodiment of an exterior surface of the monitoring device of FIG. 1 unattached to a user's hand.

As shown in FIG. 4, the display member 40 is preferably angled at an angle ranging form 20 to 70 degrees relative to the wrist edge 96 of the article 25, more preferably ranging from 30 to 60 degrees relative to the wrist edge 96, and most preferably 45 degrees relative to the wrist edge 96. The angling of the display member 40 allows for easier viewing of the real-time information by the user.

In an alternative embodiment, a short range wireless transceiver is included in the circuitry assembly 35 for transmitting information processed from the pulse oximetry device 30 to a handheld device or a computer, not shown, to form a system. The display member 40 is optional in this embodiment.

The short-range wireless transceiver is preferably a transmitter operating on a wireless protocol, e.g. Bluetooth™, part-15, or 802.11. "Part-15" refers to a conventional low-power, short-range wireless protocol, such as that used in cordless telephones. The short-range wireless transmitter (e.g., a Bluetooth™ transmitter) receives information from the microprocessor and transmits this information in the form of a packet through an antenna. The external laptop computer or hand-held device features a similar antenna coupled to a matched wireless, short-range receiver that receives the packet. In certain embodiments, the hand-held device is a cellular telephone with a Bluetooth circuit integrated directly into a chipset used in the cellular telephone. In this case, the cellular telephone may include a software application that receives, processes, and displays the information. The secondary wireless component may also include a long-range wireless transmitter that transmits information over a terrestrial, satellite, or 802.11-based wireless network. Suitable networks include those operating at least one of the following protocols: CDMA, GSM, GPRS, Mobitex, DataTac, iDEN, and analogs and derivatives thereof. Alternatively, the handheld device is a pager or PDA.

A general method of using the monitoring device 20 begins with the light source 135 transmitting red and/or infrared light through a thumb of the user. The photo-detector 130 detects the light. The pulse rate is determined by the signals received by the photo-detector 130. The ratio of the fluctuation of the red and/or infrared light signals is used to calculate the blood oxygen saturation level of the user. An optical sensor 30 with a photodetector 130 and single LED 135 is preferably utilized. Alternatively, a pulse oximetry device with two LEDs and a photodetector is utilized. Next, this information is sent to pulse oximetry board in the circuitry assembly 35 for creation of blood oxygenation level, pulse rate, signal strength bargraph, plethysmogram and status bits data. Next, the microprocessor further processes the information to display pulse rate, blood oxygenation levels, calories expended by the user of a pre-set time period, target zones of activity, time and dynamic blood pressure. Next, the information is displayed on the display member.

In a preferred embodiment, the circuit assembly housing has three control buttons 43*a*-*c*. The control buttons 43*a*-*c* are preferably positioned in relation to the display member 40 to allow the user immediate visual feedback of the user's inputted information. The middle control button 43*b* preferably activates the article 25, allows for the user's personal data to be entered and for choices to be selected by the user. The left button 43*a* preferably allows for the user's calories burned to be displayed on the display member 40 and for the activity to be reset. The right button 43*c* preferably allows for other fitness monitoring features to be displayed.

In using the article 25, the optical sensor 35 should be preferably placed on the fleshy tip of the users fingertip of the user's thumb. The thumb attachment means should be wrapped around the thumb to secure the thumb portion on the user's thumb. Alternatively, the optical sensor 35 is worn at the base of the user's thumb. When the article 25 is used during running or walking, it is best to maintain the user's hand in a relaxed and naturally at rest position.

To activate the article 25, the middle button 43*b* is depressed for preferably 0.5 seconds and the n released. The display member will appear with a current pulse of the user and a calories burned display. The microprocessor preferably stores the calories burned and accumulates the values for a daily calories burned value and a total calories burned value until the activity is reset.

To enter the user's personal data, the middle button 43*b* is depressed for 2 seconds and then released. The user will enter gender, age, mass, height and resting heart rate. Entering the data entails pushing the middle button to select a category (gender, age, . . . ) and then pushing the right or left button to scroll through the available options or to enter a value (e.g. age of the user). The middle button 43*b* is pressed again to save the entry. This process is preformed until the user's has entered all of the data that the user wishes to enter into the microprocessor. The display member 40 will then display a heart rate and current calories burned value. A preset resting heart rate for men and women is preferably stored on the microprocessor, and used as a default resting heart rate. However, the user may enter their own resting heart rate value if the user is aware of that value. To access daily calories, the left button 43*a* is pushed by the user and the display member 40 will illustrate the value for daily calories burned by the user. If the left button 43*a* is pushed again, the value for total calories burned by the user will be displayed on the display member 40. The left button 43*a* is pushed again to return to a heart rate value on the display member 40.

The right button 43*c* is pushed to scroll through the choices of other output values, which comprises: basal metabolic rate; average heart rate; minimum heart rate; maximum heart rate; fat burn heart rate exercise target zone; cardio burn heart rate exercise target zone; and, summary of daily calories burned. The basal metabolic rate (displayed as "BMR") is an estimate of the total calories burned by the user in one day without exercise, and is based on the user inputted personal data. The average heart rate (displayed as "avHR") is the average heart rate of the user between resets, and is an overall indicator of fitness. The lower the average heart rate, the healthier the heart. The average heart rate is also a measure of the effectiveness of the exercise program employed by the user since a decrease in the average heart rate of the user will indicate the user's fitness has improved. The minimum heart rate (displayed as "mnHR") of the user is typically measured during sleep and periods of relaxation. The maximum heart rate (displayed as "mxHR") is typically measured during intense workouts. The fat burn heart rate exercise target zone (displayed as "fatB") displays a low and high range for the heart rate of the user to optimize fat burning during exercise. The cardio burn heart rate exercise target zone provides a high and low range for the heart rate of the user to optimize cardio conditioning during exercise. The summary of daily calories burned (displayed as "cal") displays the daily calories burned by the user.

As mentioned above, the control component 43 allows a user to scroll and select from terms displayed on the display member 40. User inputs preferably include age, gender, weight, height and resting heart rate which can be inputted and stored in a memory of the circuit assembly 35. The real time heart rate of the user is preferably displayed as a default display, and the user's real time heart rate is preferably updated every ten seconds based on measurements from the optical sensor 30. Based on the user inputs, the calories expended by the user for a set time period are calculated and displayed on the display member 40 as desired by the user using the control component 43. The monitoring device 20 will also preferably include a conventional stop watch function, which is displayed on the display member 40 as desired by the user. The display member 40 preferably displays a visual alert when a user enters or exits a target zone such as a cardio zone or fat burning zone. The monitoring device 20 optionally includes an audio alert for entering or exiting such target zones.

The user can use the control means 43 to maneuver between the user's real-time heart rate and real time calories expended by the user during a set time period. The user can also scroll through a menu-like display on the display member 40 and enter options by pushing downward on the control component 43. The options can preferably include a "My Data" section which the user inputs by scrolling and selection an option by pushing downward, such as selecting between male and female for gender. The user can also select target zones by scrolling through a different section of the menu. As discussed below, each target zone is calculated using a formula based upon the user's personal data. In operation, when a specific target zone is selected, a visual alert in the form of a specific display such as an icon-like picture is displayed on the display member 40 to demonstrate that the user is now in the specified target zone. The icon preferably blinks for a set period of time such as ten seconds. Those skilled in the pertinent art will recognize that other options may be included on the menu-like display without departing from the spirit and scope of the present invention.

In yet an alternative embodiment, an accelerometer, not shown, is embedded within the main body 95 of the article 25 and connected to the circuitry assembly 35 in order to provide information on the distance traveled by the user. In a preferred embodiment, the accelerometer is a multiple-axis accelerometer, such as the ADXL202 made by Analog Devices of Norwood, Mass. This device is a standard micro-electronic-machine ("MEMs") module that measures acceleration and deceleration using an array of silicon-based structures.

In yet another embodiment, the monitoring device 20 comprises a first thermistor, not shown, for measuring the temperature of the user's skin and a second thermistor, not shown, for measuring the temperate of the air. The temperature readings are displayed on the display member 40 and the skin temperature is preferably utilized in further determining the calories expended by the user during a set time period. One such commercially available thermistor is sold under the brand LM34 from National Semiconductor of Santa Clara, Calif. A microcontroller that is utilized with the thermistor is sold under the brand name ATMega 8535 by Atmel of San Jose, Calif.

The microprocessor 41 can use various methods to calculate calories burned by a user. One such method uses the Harris-Benedict formula. The Harris-Benedict formula uses the factors of height, weight, age, and sex to determine basal metabolic rate (BMR). This equation is very accurate in all but the extremely muscular (will underestimate calorie needs) and the extremely overweight (will overestimate caloric needs) user.

The equations for men and women are set forth below:

Men: BMR=66+(13.7×mass (kg))+(5×height (cm))−(6.8×age (years))

Women: BMR=655+(9.6×mass)+(1.8×height)−(4.7×age)

The calories burned are calculated by multiplying the BMR by the following appropriate activity factor: sedentary; lightly active; moderately active; very active; and extra active.

Sedentary=BMR multiplied by 1.2 (little or no exercise, desk job)

Lightly active=BMR multiplied by 1.375 (light exercise/sports 1-3 days/wk)

Moderately Active=BMR multiplied by 1.55 (moderate exercise/sports 3-5 days/wk)

Very active=BMR multiplied by 1.725 (hard exercise/sports 6-7 days/wk)

Extra Active=BMR multiplied by 1.9 (hard daily exercise/sports & physical job or 2× day training, marathon, football camp, contest, etc.)

Various target zones may also be calculated by the microprocessor. These target zones include: fat burn zone; cardio zone; moderate activity zone; weight management zone; aerobic zone; anaerobic threshold zone; and red-line zone.

Fat Burn Zone=(220−age)×60% & 70%

An example for a thirty-eight year old female:

(220−38)×0.6=109

(220−38)×0.7=127

Fat Burn Zone between 109 to 127 heart beats per minute.

Cardio Zone=(220−your age)×70% & 80%

An example for a thirty-eight year old female:

(220−38)×0.7=127

(220−38)×0.8=146

Cardio zone is between 127 & 146 heart beats per minute.

Moderate Activity Zone, at 50 to 60 percent of your maximum heart rate, burns fat more readily than carbohydrates. That is the zone one should exercise at if one wants slow, even conditioning with little pain or strain.

Weight Management Zone, at 60 to 70 percent of maximum, strengthens ones heart and burns sufficient calories to lower one's body weight.

Aerobic Zone, at 70 to 80 percent of maximum, not only strengthens one's heart but also trains one's body to process oxygen more efficiently, improving endurance.

Anaerobic Threshold Zone, at 80 to 90 percent of maximum, improves one's ability to rid one's body of the lactic-acid buildup that leads to muscles ache near one's performance limit. Over time, training in this zone will raise one's limit.

Red-Line Zone, at 90 to 100 percent of maximum, is where serious athletes train when they are striving for speed instead of endurance.

EXAMPLE ONE

Female, 30 yrs old, height 167.6 centimeters, weight 54.5 kilograms.

The BMR=655+523+302−141=1339 calories/day.

The BMR is 1339 calories per day. The activity level is moderately active (work out 3-4 times per week). The activity factor is 1.55. The TDEE=1.55×1339=2075 calories/day. TDEE is calculated by multiplying the BMR of the user by the activity multiplier of the user.

A system may use the heart rate to dynamically determine an activity level and periodically recalculate the calories burned based upon that factor. An example of such an activity level look up table might be as follows:

Activity/Intensity Multiplier Based on Heart Rate

Sedentary=BMR×1.2 (little or no exercise, average heart rate 65-75 bpm or lower)

Lightly active=BMR×3.5 (light exercise, 75 bpm-115 bpm)

Mod. active=BMR×5.75 (moderate exercise, 115-140 pm)

Very active=BMR×9.25 (hard exercise, 140-175 bpm)

Extra active=BMR×13 (175 bpm-maximum heart rate as calculated with MHR formula)

For example, while sitting at a desk, a man in the above example might have a heart rate of between 65 and 75 beats per minute (BPM). (The average heart rate for an adult is between 65 and 75 beats per minute.) Based on this dynamically updated heart rate his activity level might be considered sedentary. If the heart rate remained in this range for 30 minutes, based on the Harris-Benedict formula he would have expended 1.34 calories a minute×1.2 (activity level)×30 minutes, which is equal to 48.24 calories burned.

If the man were to run a mile for 30 minutes, with a heart rate ranging between 120 and 130 bpm, his activity level might be considered very active. His caloric expenditure would be 1.34 calories a minute×9.25 (activity level)×30 minutes, which is equal to 371.85.

Another equation is weight multiplied by time multiplied by an activity factor multiplied by 0.000119.

Figure 13:
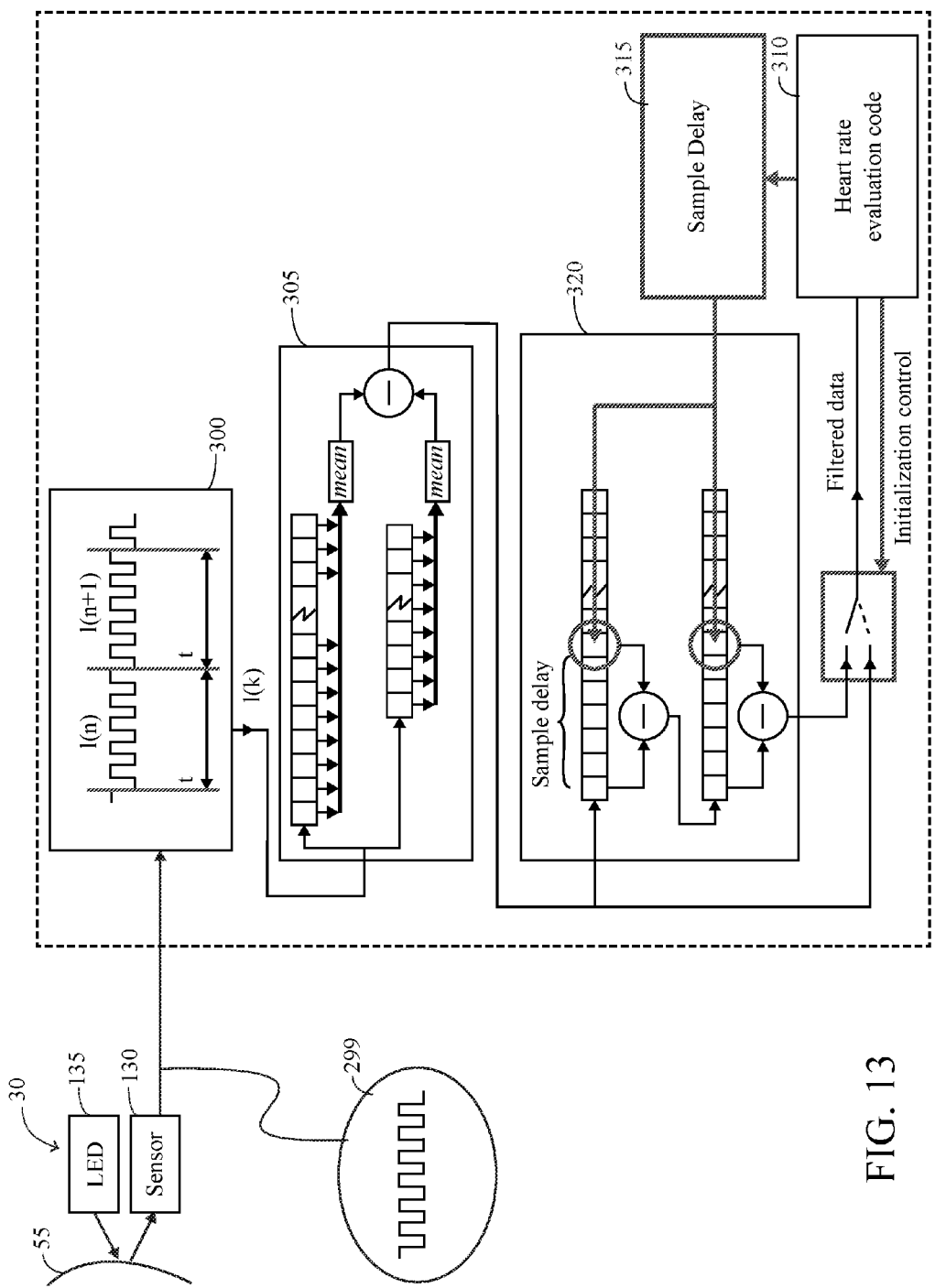
FIG. 13 is a schematic flow chart of a method of monitoring.

FIG. 13 illustrates a schematic diagram flow chart of a method of the present invention. As shown in FIG. 13, the photodetector 130 of the optical sensor 30 receives light from the light source 135 while in proximity to the user's thumb 55. The photodetector 130 digitizes the signal (light-to-voltage or light-to-frequency) and transmits a digital signal 299 to the microprocessor 41. At block 300, a counting function of the microprocessor 41 computes the number of pulses within a set time period. A preferred time period 16 milliseconds, however those skilled within the pertinent art will recognize that other time periods may be utilized without departing from the scope and spirit of the invention. The values of 1(k) are the samples of the digital signal which are proportional to the frequency and light intensity.

At block 305, a band pass filter is implemented preferably with two sets of data. At block 305, an average of the number of pulses within each of a first set of time periods is calculated by the microprocessor 41. For example, the number of pulses within forty-four sequential time periods are summed and then divided by forty-four to generate an average pulse value for the first set of time periods. Next, an average of the number of pulses within each of a second set of time periods is calculated by the microprocessor 41. For example, the number of pulses within twenty-two sequential time periods are summed and then divided by twenty-two to generate an average pulse value for the second set of time periods. Preferably, the second set of time periods is less than the first set of time periods. Next, the average pulse value of the second set of time periods is subtracted from the average pulse value for the first set of time periods to generate a first filtered pulse data value.

At block 310, the filtered pulse data value is processed using a heart rate evaluation code to generate a first heart rate value. In a preferred method, the heart rate evaluation code obtains the heart rate by calculating the distance between crossing points of a data value of a heart rate waveform through zero. Once the first heart rate value is known, then an adaptive resonant filter is utilized to generate a filtered second heart rate value by attenuating interference caused by artifacts. At block 315, a sample delay is computed as the period of evaluated heart rate divided by two.

At block 320, preferably a two cascade adaptive resonant filter generates a second filtered pulse data value which is processed at block 310 using the heart rate evaluation code to generate a second heart rate value. Those skilled in the pertinent art will recognize that three, four, or more cascade adaptive resonant filters may be utilized in generating the second filtered pulse data value. Essentially, the highest and lowest values are disregarded in calculating the filtered second heart rate value. Alternatively, a phase is established and any values outside of the phase are disregarded in calculating the second heart rate value. The filtering is preferably continued during the use of the monitor thereby further refining the heart rate value of the user.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention the following:

1. A device for monitoring a user's real-time heart rate, the device comprising:
    a processor;
    an optical sensor adapted for placement in proximity to the artery of the user;
    a control component; and
    a display member;
    wherein the optical sensor is configured to generate a digital signal corresponding to the flow of blood through an artery of the user;
    wherein the processor is configured to process the digital signal to obtain an average pulse value of a first set of time periods, wherein a pulse of the average pulse value is a pulse output of a light to frequency conversion process;
    wherein the processor is configured to process the digital signal to obtain an average pulse value of a second set of time periods, the second set of time periods less than the first set of time periods, wherein the second set of time periods is overlapping to the first set of time periods;
    wherein the processor is configured to subtract the average pulse value of the second set of time periods from the average pulse value of the first set of time periods to generate a first filtered pulse data value;
    wherein the processor is configured to process the first filtered pulse data value to obtain a first heart rate value;
    wherein the processor is configured to use the first heart rate value to filter the subsequent average pulse values generated from the digital signal to obtain a real-time heart rate value of the user;
    wherein the processor is configured to process the real-time heart rate data of the user and inputted user data for age, gender, height and weight for analysis of calories expended by the user over a set time period, and for real-time display of a plurality of the user's vital signs; and
    wherein the display is configured to display the plurality of user's vital signs on the display member disposed on an exterior surface of the device, the display of the plurality of user's vital signs controlled by the user using the control component.

2. The device according to claim 1 further comprising an accelerometer, wherein the accelerometer is configured to measure the distance traveled by the user during a time period, and displaying the distance traveled by the user on the display member.

3. The device according to claim 1 wherein the optical sensor is a light-to-frequency photodetector capable of transmitting a digital signal, and at least one light emitting diode capable of radiating light ranging from 600 nanometers to 1100 nanometers.

4. The device according to claim 1 wherein the display member comprises a light emitting diode array having a plurality of columns and a plurality of rows, each of the plurality of columns capable of separate illumination to provide the appearance of a moving display.

* * * * *